United States Patent
Aassveen et al.

(10) Patent No.: US 9,132,163 B2
(45) Date of Patent: Sep. 15, 2015

(54) METHOD FOR PURIFICATION OF MICAFUNGIN

(75) Inventors: Lene Aassveen, Oslo (NO); Eli Karin Dale, Oslo (NO); Espen Fridtjof Hansen, Lommedalen (NO); Kjersti Meldahl Eide, Oslo (NO)

(73) Assignee: XELLIA PHARMACEUTICALS APS (DK), `

( * ) Notice: Subject to any disclaimer, the term of this patent is extended or adjusted under 35 U.S.C. 154(b) by 0 days.

(21) Appl. No.: 14/110,477

(22) PCT Filed: Apr. 13, 2012

(86) PCT No.: PCT/EP2012/056768
§ 371 (c)(1),
(2), (4) Date: Nov. 13, 2013

(87) PCT Pub. No.: WO2012/143293
PCT Pub. Date: Oct. 26, 2012

(65) Prior Publication Data
US 2014/0371423 A1    Dec. 18, 2014

Related U.S. Application Data

(60) Provisional application No. 61/477,190, filed on Apr. 20, 2011.

(51) Int. Cl.
*C07K 7/56* (2006.01)
*A61K 38/08* (2006.01)
*A61K 31/4164* (2006.01)
*B01D 15/32* (2006.01)
*A61K 38/00* (2006.01)

(52) U.S. Cl.
CPC ............ *A61K 38/08* (2013.01); *A61K 31/4164* (2013.01); *B01D 15/327* (2013.01); *C07K 7/56* (2013.01); *A61K 38/00* (2013.01)

(58) Field of Classification Search
None
See application file for complete search history.

(56) References Cited

U.S. PATENT DOCUMENTS

| | | |
|---|---|---|
| 5,202,309 A | 4/1993 | Schwartz et al. |
| 6,107,458 A | 8/2000 | Ohki et al. |
| 6,170,458 B1 | 1/2001 | Miller |
| 6,506,726 B1 | 1/2003 | Dobbins et al. |
| 7,199,248 B2 | 4/2007 | Tsuboi et al. |
| 2008/0108806 A1* | 5/2008 | Keri et al. ............... 540/460 |

FOREIGN PATENT DOCUMENTS

| | | |
|---|---|---|
| EP | 2236513 A1 | 10/2010 |
| WO | 2012041218 A1 | 4/2012 |
| WO | 2012041801 A1 | 4/2012 |

OTHER PUBLICATIONS

Ohigashi et al.; "General Thesis: Process Development of Micafungin, a Novel Lipopeptide Antifungal Agent"; Journal of Synthetic Organic Chemistry, Japan; 64(12) pp. 58-67; with English Machine Translation; (2006).
International Search Report and Written Opinion: International Application No. PCT/EP2012/056768; International Filing Date Apr. 13, 2012; Date of Mailing Jun. 15, 2012; Applicant's File Reference No. P22555PC; 12 pages.
DIAION_Product Line Brochure from Mitsubishi Chemical Corporation; ontained on line http://www.resindion.com; printed Mar. 10, 2015.

* cited by examiner

*Primary Examiner* — Jeffrey E Russel
(74) *Attorney, Agent, or Firm* — Cantor Colburn LLP (57) ABSTRACT

The present invention relates to a method for the purification of Micafungin. Specifically, a method is provided in which a micafungin starting material containing a first micafungin salt is adsorbed to a solid support, the adsorbed micafungin salt is washed with an aqueous solution comprising a dissolved second salt, the second micafungin salt is eluted using a water miscible organic solvent.

24 Claims, 9 Drawing Sheets

ELUTION PROFILE OF DIPEA AND MICA ON HP20SS
10% MeOH IN LOAD, SALT WASH WITH
3M NaCl/0.1M NaAc:METHANOL (90:10)

| CV | SOLUTION | DIPEA (mg/ml) |
|---|---|---|
| 0 | MICAFUNGIN – DIPEA DISSOLVED IN 10% MeOH/90% RO WATER | |
| 1 | | 0 |
| 2 | | 2.756 |
| 3 | | 1.827 |
| 4 | | 0.787 |
| 5 | 90% 3M NaCl/0.1M NaAc, 10% MeOH | 0.445 |
| 6 | | 0.258 |
| 7 | | 0.169 |
| 8 | | 0.111 |
| 9 | | 0.040 |
| 10 | | 0.022 |
| 11 | 40% MeOH | 0.018 |
| 12 | | 0.014 |
| 16 | | 0 |
| 18.2 | 90% MeOH | 0.004 |

Fig. 3

ELUTION PROFILE OF DIPEA AND MICA ON HP20SS 10% MeOH IN LOAD, SALT WASH WITH 3M NaCl/0.1M NaAc

| CV | SOLUTION | DIPEA (mg/ml) |
|---|---|---|
| 0 | MICAFUNGIN - DIPEA DISSOLVED IN 10% MeOH/90% RO WATER | |
| 1 | | 0 |
| 2 | | 0.413 |
| 3 | | 0.848 |
| 4 | | 0.739 |
| 5 | 3M NaCl/1.01M NaAc | 0.685 |
| 6 | | 0.488 |
| 7 | | 0.478 |
| 8 | | 0.364 |
| 9 | | 0.240 |
| 10 | | 0.021 |
| 11 | | 0.017 |
| 12 | 40% MeOH | 1.359 |
| 16 | | 0.003 |
| 18.5 | 90% MeOH | 0 |

| CV | SOLUTION | DIPEA (mg/ml) |
|---|---|---|
| 0 | MICAFUNGIN – DIPEA DISSOLVED IN 10% MeOH/90% RO WATER | |
| 1 | | 0.040 |
| 2 | | 2.126 |
| 3 | | 0.285 |
| 4 | | 0.005 |
| 5 | 60% 3M NaCl/0.1M NaAc, 40% MeOH | 0 |
| 6 | | 0 |
| 7 | | 0 |
| 8 | | 0 |
| 9 | | 0 |
| 10 | | 0 |
| 11 | 40% MeOH | 0 |
| 12 | | 0 |
| 15 | | 0 |
| 17.7 | 90% MeOH | 0 |

METHOD FOR PURIFICATION OF MICAFUNGIN

CROSS-REFERENCE TO RELATED APPLICATIONS

This application is a 371 of PCT/EP2012/056768 filed Apr. 13, 2012, which claims the benefit of priority to U.S. provisional application No. 61/477,190, filed on Apr. 20, 2011, under the provisions of 35 U.S.C. 119 and the International Convention for the protection of Industrial Property, which are incorporated herein by reference.

TECHNICAL FILED

The present invention relates to an improved method for purification of a Micafungin salt, in particular Micafungin sodium.

BACKGROUND

Micafungin is the active pharmaceutical ingredient in Mycamine®. According to the FDA label, the chemical structure of Micafungin sodium is represented by formula (I):

Micafungin is also known as Pneumocandin A0, 1-[(4R, 5R)-4,5-dihydroxy-N2-[4-[5-[4-(pentyloxy)phenyl]-3-isoxazolyl]benzoyl]-L-ornithine]-4-[(4S)-4-hydroxy-4-[4-hydroxy-3-(sulfoxy)phenyl]-L-threonine]. Micafungin sodium is furthermore known as FK-463. The assigned Registry No's by Chemical Abstracts are 235114-32-6 for Micafungin and 208538-73-2 for Micafungin sodium.

Micafungin is an echinocandin which inhibits 1,3-β-D-glucan synthase and thus leads to fungal cell lysis. Micafungin is thus useful as an antifungal agent in the treatment of infections caused by strains of e.g. *Aspergillus, Cryptococcus, Candida, Mucor, Actinomyces, Histoplasma, Dermatophyte, Malassezia*, and *Fusarium*. Micafungin is the active ingredient in the approved drugs Mycamine® and Funguard® which are used in the treatment and prophylaxis of infections caused by *Candida*.

Various methods for the preparation and purification of Micafungin are known to the skilled person, see e.g. U.S. Pat. No. 6,107,458 and U.S. Pat. No. 7,199,248. More particularly, U.S. Pat. No. 7,199,248 discloses a method wherein a crude DIPEA salt of Micafungin is purified by filtration and chromatographic separation using a regenerated γ Alumina in a 1350-L column and eluting Micafungin DIPEA with Methanol. The Micafungin containing fraction is further purified and transferred to a sodium salt of Micafungin, inter alia by ion exchange chromatography using a regenerated ion exchange resin UBK510L. Micafungin sodium is eluted with aqueous Methanol. Acetone and ethyl acetate is finally used for precipitation of Micafungin sodium.

It is well known in the art that the diisopropylethylamine (DIPEA) salt of Micafungin is more stable than the sodium salt of Micafungin. Therefore, the prior art methods as the method disclosed above often make use of the DIPEA salt as an intermediate when preparing Micafungin sodium. This is e.g. described in the General Thesis, "Process Development of Micafungin, a Novel Lipopeptide Antifungal Agent" by Ohigashi et al. in Journal of Synthetic Organic Chemistry, Japan, vol. 64, No. 12, December 2006. In Ohigashi et al., a method is disclosed wherein impurities present in a DIPEA salt of Micafungin are removed by the use of resins. The DIPEA salt purified by the use of an alumina resin column is according to Ohigashi et al. then subjected to ion exchange chromatography for converting the DIPEA salt of Micafungin to a sodium salt of Micafungin.

It is clear that the prior art methods for the preparation of Micafungin sodium as mentioned above involves two consecutive chromatography steps, i.e. firstly the purification of Micafungin DIPEA on a Reverse Phase Chromatography (RPC) resin and secondly the transformation of the DIPEA salt to the sodium salt, i.e. a salt swap, on a ion-exchange resin. The use of two subsequent chromatography steps for the obtainment of the desired sodium salt of Micafungin is labor-intensive and the providing of an improved method involving fewer processing steps, less chemicals and equipment would be beneficial both from an economical aspect as well as from an environmental and labor-saving point of view.

It is thus still a need for more efficient processes for the preparation of a purified Micafungin and derivates thereof, such as the sodium salt of Micafungin.

SUMMARY OF THE INVENTION

The object of the present invention is to provide an improved process for the purification of a salt of Micafungin, such as Micafungin sodium.

As mentioned above, the prior art methods is inter alia attended with the disadvantage of two consecutive chromatography steps. The present invention is based on the surprising findings that the two steps (salt swap and purification) can be performed in the one and same operation. The process of the present invention thus involves several self-evident advantages, both of environmental and economical character, such as reduced consumption of chemicals, shorter process times and the use of less hardware requirements.

According to one embodiment of the invention, a method for producing a pharmaceutically acceptable Micafungin salt is provided wherein said process comprises the steps of:

a) applying a Micafungin starting material to a hydrophobic adsorbent resin support;
b) exposing the bound Micafungin to an aqueous solution of a dissolved pharmaceutically acceptable salt;
c) eluting the dissolved pharmaceutically acceptable salt of Micafungin with a solution comprising a water miscible organic solvent;
provided that at least one of
  i) the starting material in step a)
  ii) or the aqueous solution in step b)
comprises a water miscible organic solvent.

According to one aspect of the above embodiment, a method is provided which further comprises a step wherein the bound Micafungin of step b) is further exposed to an aqueous solution comprising a water miscible organic solvent one or more times for the removal of impurities.

According to another aspect of the above embodiment, a method is provided wherein the starting material in step a) comprises a water miscible organic solvent in the range of 0-30% v/v.

According to another aspect of the above embodiment, a method is provided wherein the starting material in step a) comprises a water miscible organic solvent in the range of 5-15% v/v.

According to another aspect of the above embodiment, a method is provided wherein the starting material in step a) comprises a water miscible organic solvent in the range of 10% v/v.

According to another aspect of the above embodiment, a method is provided wherein the aqueous solution in step b) comprises a water miscible organic solvent in the range of 0-40% v/v.

According to another aspect of the above embodiment, a method is provided wherein the aqueous solution in step b) comprises a water miscible organic solvent in the range of 20% v/v.

According to another aspect of the above embodiment, a method is provided wherein the water miscible organic solvent is selected from the group consisting of branched or non-branched C1-C3 alcohols, C3-C6 ketones and polar aprotic organic solvents.

According to another aspect of the above embodiment, a method is provided wherein the water miscible organic solvent is selected from the group consisting of methanol, ethanol, propanol, isopropanol, acetone and acetonitrile.

According to another aspect of the above embodiment, a method is provided wherein the aqueous solution in step c) comprises at least 30% v/v acetonitrile as a water miscible organic solvent.

According to another aspect of the above embodiment, a method is provided wherein the water miscible organic solvent is methanol.

According to another aspect of the above embodiment, a method is provided wherein the aqueous solution in step c) comprises at least 70% v/v methanol, such as at least 90% v/v methanol, such as at least 95% v/v methanol as a water miscible organic solvent.

According to another aspect of the above embodiment, a method is provided wherein the starting material in step a), the aqueous solution in step b) and the washing solution in step c) comprises a water miscible organic solvent.

According to another embodiment of the invention, a method for producing a pharmaceutically acceptable Micafungin salt is provided wherein said process comprises the steps of:

a) applying a Micafungin starting material to a hydrophobic adsorbent resin support;
b) exposing the bound Micafungin to an aqueous solution of a dissolved pharmaceutically acceptable salt;
c) optionally exposing the bound salt of Micafungin obtained in b) to an aqueous solution comprising a water miscible organic solvent one or more times for the removal of impurities;
d) eluting the dissolved pharmaceutically acceptable salt of Micafungin with a solution comprising a water miscible organic solvent;
provided that when step c) is not performed, then the Micafungin starting material and/or the aqueous solution in step b) comprises a water miscible organic solvent.

According to one embodiment, the Micafungin starting material or the aqueous solution in step b) of the present method comprises 2-30% v/v of a water miscible organic solvent.

According to one embodiment, the Micafungin starting material and the aqueous solution in step b) of the present method comprises 2-30% v/v of a water miscible organic solvent.

According to one embodiment, the aqueous solution in step c) of the present method comprises 30-50% v/v of a water miscible organic solvent.

According to another embodiment, the cation present in the Micafungin starting material of the present invention is DIPEA.

According to yet another embodiment, the resin used according to the present method is HP20SS.

According to another embodiment, the Micafungin starting material and the aqueous solution in step b) of the present method comprises a water miscible organic solvent.

According to yet another embodiment, the Micafungin starting material and the aqueous solution in step b) of the present method comprises Methanol.

According to yet another embodiment of the present method, the water miscible organic solvent present in the Micafungin starting material and/or the aqueous solution in step b) is Methanol.

According to yet another embodiment of the present method, the aqueous solution in step b) comprises Methanol.

According to a final embodiment of the present invention, a method is provided wherein the pharmaceutically acceptable salt of Micafungin is the sodium salt, and the resin is HP20SS, and the Micafungin starting material comprises Micafungin DIPEA and 10% v/v Methanol, and the solution in step b) comprises 20% v/v Methanol and 80% v/v 3M NaCl, 0.1M NaCH$_3$COO and the solution in step c) comprises 40% v/v Methanol and the solution in step d) comprises 90% v/v Methanol.

DETAILED DESCRIPTION

According to the present invention, Micafungin is any compound comprising the structure (I)

or salts thereof. The expression "salts thereof" is meant to embrace any salts of Micafungin that may be useful for the purpose of preparation and/or purification of Micafungin or any pharmaceutically acceptable salts of Micafungin useful as an active ingredient in a medicinal formulation. In this respect, a non-limiting list of salts of Micafungin is the sodium salt, the potassium salt, the diisopropylethylamine (DIPEA) salt, etc.

Micafungin is a semisynthetic derivative of FR901379, a fermentation product obtained from *Coleophoma empetri* F-11899 (deposited as FERM BP-2635).

Micafungin may be prepared by deacylation of the fermentation product FR901379, obtaining a compound named the Micafungin peptide core herein, and subsequent coupling of the Micafungin side chain, 4-[5-(4-pentyloxyphenyl)isoxazole-3-yl]benzoic acid, to said peptide core. The Registry Number of the said side chain assigned by Chemical abstracts is 179162-55-1. It is also known by the name FR195752.

Deacylation of FR901379 can be performed by enzymes produced by certain microorganisms of the Actinoplanaceae, for example, *Actinoplanes utahensis* 1F0-13244, *Actinoplanes utahensis* ATCC 12301, *Actinoplanes missourienses* NRRL 12053. The deacylated peptide core is represented here as formula II. The sodium salt of the deacylated peptide core was named FR133303 (see EP462531).

Reacylation of the peptide core represented by formula II can be performed as disclosed in U.S. Pat. No. 7,199,248.

The Micafungin peptide core is represented by the formula II.

II

According to the present invention, a method for the preparation of a purified salt of Micafungin is provided. According to one embodiment of the invention, the salt of Micafungin obtained according to the present invention is the sodium salt of Micafungin. It is to be understood that also other pharmaceutically acceptable salts of Micafungin may be obtained by the present method, such as e.g. the potassium salt of Micafungin.

According to the present invention, a method is provided for the purification and preparation of a pharmaceutically acceptable salt of Micafungin wherein a Micafungin starting material is adsorbed to a solid support, subjecting and washing the adsorbed Micafungin with an aqueous solution comprising a dissolved salt and finally eluting the so obtained pharmaceutically acceptable salt of Micafungin using an elution solution comprising a water miscible organic solvent.

According to the present invention, the term "Micafungin starting material" is an aqueous solution comprising a dissolved salt of Micafungin. The Micafungin starting material enables the adsorption of the Micafungin salt to a solid support in such a way that both salt swap and purification may be performed in one step.

The Micafungin starting material comprises a salt of Micafungin suitable for the adsorption to a solid support. When said salt is adsorbed to a solid support and upon the further exposure to a solution of a dissolved pharmaceutically acceptable salt, a salt swap is enabled. The initial cations associated with Micafungin in the Micafungin starting material can then be removed by washing with an aqueous solution optionally comprising a water miscible organic solvent. Finally, the pharmaceutically acceptable Micafungin salt can be eluted by an aqueous solution comprising a water miscible organic solvent.

The Micafungin salt present in the starting material is thus different from the salt of Micafungin being eluted from the solid support after the salt swap and purification. The Micafungin salt present in the Micafungin starting material is according to a preferred embodiment of the invention the DIPEA salt of Micafungin.

According to one aspect of the present invention, a method is provided, wherein the final salt of Micafungin is substantially free of the cation of the Micafungin salt present in the Micafungin starting material. The term "substantially free" means in the context of the present invention that the levels of said cation in the final Micafungin salt are not detectable. The term "not detectable" means in the context of the present invention that the cation of the Micafungin starting material, e.g. DIPEA cannot be detected by the following HPLC assay:

System Parameters
Column Kinetex C18, 2.6μ, 100 mm×2.1 mm. 100 A
Flow rate 0.8 mL/min
Column temperature 30° C.
Back pressure approximately 3500 psi or 250 bar
Mobile phase A 99% MilliQ water,
  1% Acetonitrile,
  0.1% (v/v) TFA
Mobile phase B 1% MilliQ water,
  99% Acetonitrile,
  0.1%(v/v) TFA
Gradient

| Time (min) | % B |
|---|---|
| 0 | 0 |
| 5 | 15 |
| 6 | 50 |
| 7 | 50 |
| 8 | 0 |
| 15 | 0 |

Run Time 15 min

Injection volume 5 μL

Auto sampler temperature 5° C.

Integrator setting Peak area %.

Retention time, Dipea: approx. 4.6 minutes

Detector: Corona Cad detector

Sample preparation:

Accurately weigh 50 mg of the sample into a 10 ml volumetric flask.

Dissolve in and dilute to volume with dilution solution (water with 0.1% TFA). Inject. 5 μl.

According to another aspect of the present invention, a method is provided, wherein the final salt of Micafungin is sufficiently free of the cation of the Micafungin salt present in the Micafungin starting material. The term "sufficiently free" means in the context of the present invention that the level of the cation from the Micafungin starting material remaining in the final Micafungin salt is below 300 ppm. E.g. according to one embodiment of the present method, the level of DIPEA in the produced Micafungin sodium is less than 300 ppm.

According to one aspect of the present invention, a method for producing Micafungin sodium is provided, wherein the obtained Micafungin sodium is substantially free of DIPEA.

According to one aspect of the present invention, a method for producing Micafungin sodium is provided, wherein the obtained Micafungin sodium is sufficiently free of DIPEA.

According to yet another aspect of the invention, the Micafungin starting material is an aqueous solution of a dissolved salt of Micafungin which in addition comprises a water miscible organic solvent. The presence of a water miscible organic solvent will further facilitate the adsorption of the Micafungin salt present in the Micafungin starting material to a solid support in such a way that both purification and salt swap may be performed in one step. More particularly, the Micafungin starting material may comprise an aqueous solution of dissolved Micafungin diisopropylethylamine (DIPEA) and a water miscible organic solvent.

The salt of Micafungin present in the Micafungin starting material may be prepared according to methods well known to the skilled person. For example, Micafungin DIPEA of the formula may be prepared according to the methods disclosed in U.S. Pat. No. 6,107,458 or U.S. Pat. No. 7,199,248. A Micafungin salt useful as a starting material according to the present invention may also be prepared as outlined in Ohigashi et al., supra.

It is to be understood that the term "a water miscible organic solvent" that may optionally be present in the Micafungin starting material represents a solvent that further facilitates the binding of the Micafungin present in the Micafungin starting material in such a way that a salt swap may be performed in addition to the purification of Micafungin in one chromatographic step only. A non-limiting list of suitable water miscible organic solvent comprises branched or non-branched C1-C3 alcohols, C3-C6 ketones and polar aprotic organic solvents (e.g. Methanol, Ethanol, Propanol, Isopropanol, Acetone and Acetonitrile). According to one embodiment of the present invention, the water miscible organic solvent is Methanol.

The skilled person will acknowledge the proper amount of the water miscible organic solvent to be present in the Micafungin starting material based on the teaching of the present invention and his/her common general knowledge. More particularly, the skilled person will understand that any amount of the water miscible organic solvent that facilitates the binding of the Micafungin salt comprised in the starting material and the further salt swap, purification and eluting of the desired Micafungin salt may be used.

The amount of water miscible organic solvent present in the starting material will depend on the type of solvent used. According to one embodiment of the present invention, the amount of the water miscible organic solvent that may be present in the Micafungin starting material used according to the present invention is from 0-30% v/v. According to another embodiment of the present invention, the amount of the water miscible organic solvent that may be present in the Micafungin starting material used according to the present invention is from 5-15% v/v. According to yet another embodiment of the present invention, the amount of the water miscible organic solvent in the Micafungin starting material used according to the present invention is about 10% v/v.

A solid support according to the present invention may be any material enabling the adsorption of the Micafungin salt present in the starting material to said support, i.e. binding said salt through hydrophobic interaction in such a way that the bound Micafungin salt may be transferred to another salt, e.g. facilitating the transformation of Micafungin DIPEA to Micafungin sodium. Such a transformation of one salt of a compound to another salt of said compounds is commonly known as a "salt swap".

Furthermore, the solid support must also provide binding of the Micafungin salt present in the starting material in such a way that impurities may be removed in addition to said salt swap prior to the elution of the desired pharmaceutically acceptable salt of Micafungin.

Yet another characteristic of the solid support in addition to the above is that it finally must facilitate a reversible binding of the Micafungin salt at the option of the skilled person, i.e. enabling elution of the desired salt obtained after the salt swap and purification of Micafungin.

More particularly, the solid support is according to the invention a hydrophobic adsorbent resin support including but not limited to modified silica, polystyrene or acrylic materials, and including e.g. the polyamide adsorbent Polyamide C6 (Macherey Nagel), the acrylic adsorbent XAD7HP® (Rohm & Haas) or HP2MG® (Diaion), and the polystyrene divinyl benzene adsorbents XAD1600 (Rohm & Haas), HP20SS (Diaion), SP20SS (Diaion). The most preferred resin is HP20SS.

The salt swap is performed by exposing the Micafungin salt of the starting material being adsorbed to the solid support to an aqueous solution of the desired pharmaceutically acceptable salt, such as e.g. an aqueous solution of sodium or potassium salt. According to one embodiment of the invention, the adsorbed Micafungin salt, e.g. the DIPEA salt of Micafungin, is exposed to an aqueous dissolution of a NaCl and/or Na-acetate buffer with pH 4-6. The aqueous solution of a pharmaceutically acceptable salt may also include a water miscible organic solvent. The water miscible organic solvent may be the same solvent that may be present in the Micafungin starting material as defined above.

According to one embodiment, the adsorbed Micafungin salt is exposed to an aqueous solution of a pharmaceutical acceptable salt and 10% v/v methanol. According to another embodiment, the adsorbed Micafungin salt is exposed to an aqueous solution of a pharmaceutical acceptable salt comprising 20% v/v methanol. The pH of the aqueous solution of the pharmaceutically acceptable salt of Micafungin to be obtained in this step should be selected so as to avoid degradation of said Micafungin salt. Preferably the pH of said solution is acidic. For example, the pH of the aqueous solution of the dissolved pharmaceutically acceptable salt may be about 4.5.

Further purification of Micafungin may be performed by washing the solid support with a solution comprising a water miscible organic solvent either stepwise or using a gradient. E.g. a washing solution comprising 40% v/v Methanol, can remove significant amounts of impurities (such as by-products or degradation products) from the HP20SS resin. In general, by-products and degradation products with similar binding/elution properties as the desired Micafungin salt, can be selectively removed by applying a washing solution comprising a higher level of the water miscible organic solvent. In this context, "higher level" means that level of the water miscible organic solvent is higher compared with the level of water miscible organic solvent present in the Micafungin starting material or the solution comprising the pharmaceutically acceptable salt of Micafungin (i.e. step b) of the present method). The use of successive increasing levels of a water miscible organic solvent throughout the steps a)-d) of the present method presuppose that it is the same type of water miscible organic solvent used in all steps a)-d) whenever these steps includes the presence of said solvent. Reactants such as e.g. by-products and degradation products present in the starting material according to the present invention may thus be removed using higher concentrations of the same solvent as present in the Micafungin starting material.

The resulting Micafungin salt, e.g. the sodium salt of Micafungin bound to the solid support obtained through the salt swapping and optional washing (purification) step, may be eluted by applying an aqueous solution comprising a water miscible organic solvent wherein the level of the water miscible organic solvent in the elution solution is higher compared with the amount of water miscible organic solvent present in the previous steps of the present method. The water miscible organic solvent may be of the same type as present in the Micafungin starting material. I.e., a non limiting list of suitable water miscible organic solvent to be used when eluting the desired Micafungin salt from the solid support according to the present invention comprises branched or non-branched C1-C3 alcohols, C3-C6 ketones and polar aprotic organic solvents such as Methanol, Ethanol, Propanol, Iso-propanol, Acetone, and Acetonitrile. According to one embodiment of the present invention, the water miscible organic solvent is Methanol.

The amount of the water miscible organic solvent present in the elution solution is an amount being sufficient for elution of Micafungin. The amount of the water miscible organic solvent present in the elution solution will depend on the polarity of the solvent and the hydrophobicity of the hydrophobic adsorbent resin support. E.g. a pharmaceutically acceptable salt of Micafungin can be eluted from HP20SS by an aqueous solution comprising more than 30% v/v acetonitrile. A pharmaceutically acceptable salt of Micafungin can be eluted from HP20SS by an aqueous solution comprising more than 70% v/v Methanol. The skilled artisan will be able to determine the appropriate amount of the water miscible organic solvent in the aqueous elution solution based on his general knowledge of the various hydrophobic adsorbent resin support that are used according to the present invention and by routine experiments.

According to a preferred embodiment of the present invention, Micafungin sodium is eluted by applying an aqueous solution comprising Methanol at a concentration of 70%-95% v/v.

The Micafungin salt being prepared according to the present invention may be used in the manufacturing of pharmaceutical composition useful for the treatment and prevention of infectious diseases in mammals, including humans and animals. Said pharmaceutical composition may be prepared using standard techniques well known in the art. The pharmaceutical composition may also be subjected to conventional pharmaceutical operations such as sterilization.

For example, a pharmaceutical composition may be prepared in form of a dosage unit containing a given amount of purified Micafungin, alone or in combination with another active ingredient, and together with pharmaceutically acceptable excipients. The term "pharmaceutical acceptable excipient" refers to one or more formulation materials suitable for accomplishing or enhancing the delivery of Micafungin contained in the pharmaceutical composition to the patients in need thereof. A "pharmaceutical acceptable excipient" may also be represented by the presence of adjuvants, such as preservatives, stabilizers, wetting agents, emulsifiers, buffers and the like. Lactose is an example of a suitable stabilizer for Micafungin, especially in lyophilized form. The skilled person will be well aware of the various pharmaceutical excipients available for the preparation of pharmaceutical formulations comprising antifungal compounds like Micafungin. The composition according to the present invention may be prepared to enable parenteral administration, e.g. intravenous administration.

The patient in need for a composition according to the present invention may be administered a suitable dosage of Micafungin. A suitable daily dose for a human or mammal may vary widely depending on the condition of the patient and other factors. The daily dose may be determined by the skilled artisan using routine methods for determining the appropriate dose suitable for each patient, e.g. based on the doses commonly used for the treatment and prevention of infections when administering Mycamine®.

A skilled person will from the following examples acknowledge the many advantages of the present invention. The experiments and results below are to be understood to serve as non-limiting examples only.

EXAMPLES

In the following examples, a hydrophobic resin, HP20SS (Diaion), was packed into a chromatography column (15 ml, i.d 1.1 cm). 1.125 g Micafungin starting material (100 mg Micafungin/ml) was added to the column (0.5 ml/min). The column was washed with a 3M NaCl/0.1M NaAc pH 5.5 solution with or without addition of methanol (150 ml). The column was then washed with an aqueous solution comprising 40% methanol (90 ml). Micafungin sodium was eluted from the column with 90% methanol.

The 3M NaCl/0.1M NaAc pH 5.5 solution was prepared by dissolving 350.64 g NaCl in 1988.5 ml RO water and adding 11.44 ml acetic acid. pH was adjusted to 5.5 with NaOH(s).

Example 1

Organic Solvent in Load and Wash

An aqueous solution comprising crude Micafungin DIPEA salt and 10% v/v Methanol was applied to a HP20SS column.

The column was first washed with an aqueous solution comprising 90% v/v 3M NaCl/0.1M NaAc pH 5.5 and 10% v/v Methanol.

The column was then washed with an aqueous solution comprising 40% v/v Methanol.

Micafungin sodium was eluted with a solution comprising 90% v/v Methanol and 10% v/v water.

Figure 1:
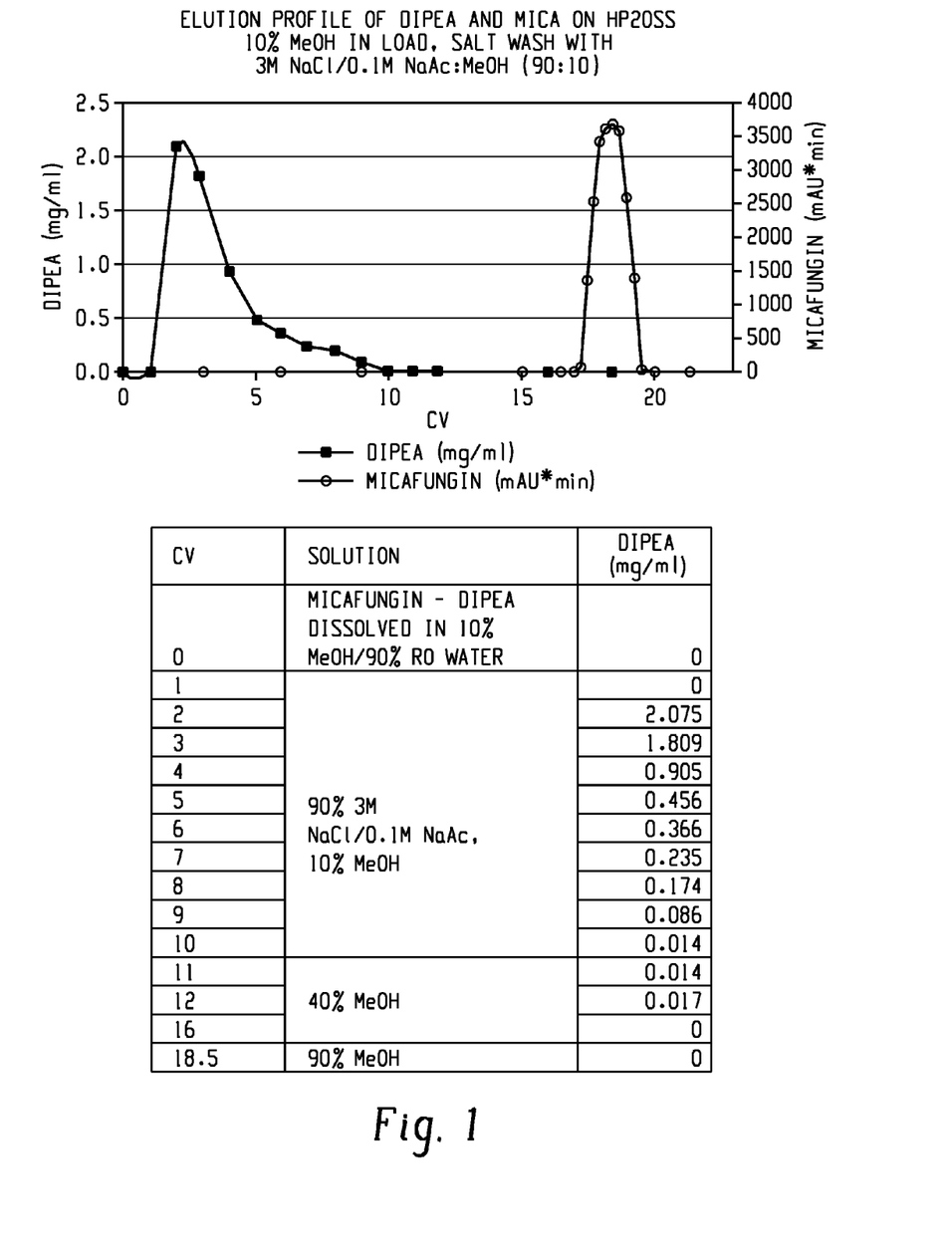
FIGS. 1-9 illustrate the elution profile of DIPEA and Micafungin sodium from HP20SS according to the corresponding Examples 1-9. The pertaining tables show the level of DIPEA in eluted fractions (CV=column volumes).

As seen in FIG. 1, the Micafungin sodium solution eluted at 18-20 CV is substantially free of DIPEA Example 2

Organic Solvent in Load

An aqueous solution comprising crude Micafungin DIPEA salt and 10% v/v Methanol was applied to a HP20SS column.

The column was washed with an aqueous solution comprising 3M NaCl/0.1M NaAc pH 5.5.

Micafungin sodium was eluted with a solution comprising 90% v/v Methanol and 10% v/v water.

Figure 2:
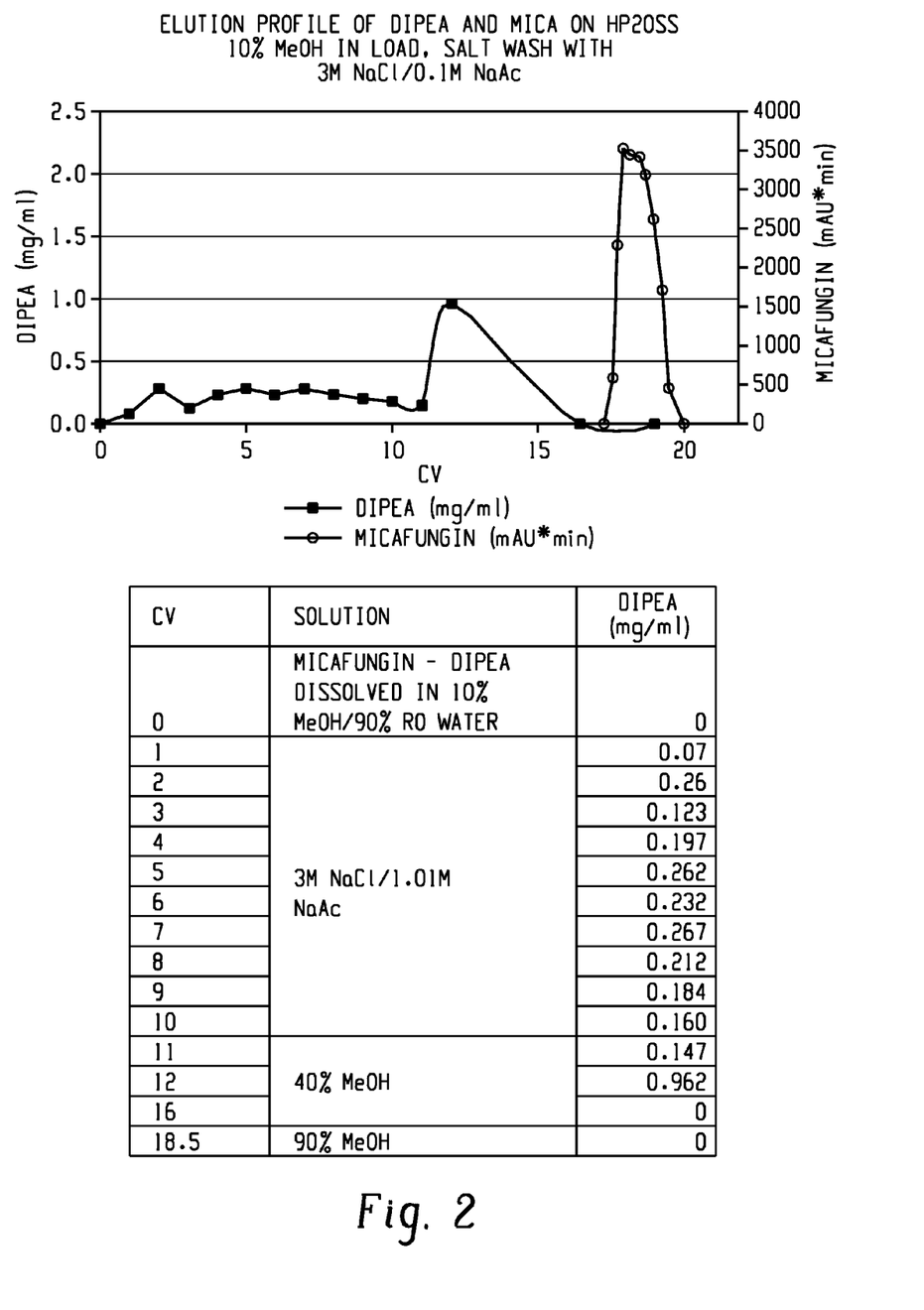

As seen in FIG. 2, the Micafungin sodium solution eluted at 18-20 CV is substantially free of DIPEA Example 3

Organic Solvent in Load and Wash

An aqueous solution comprising crude Micafungin DIPEA salt and 10% v/v Methanol was applied to a HP20SS column.

The column was first washed with an aqueous solution comprising 90% v/v 3M NaCl/0.1M NaAc pH 5.5 and 10% v/v Methanol.

The column was then washed with an aqueous solution comprising 40% v/v Methanol.

Micafungin sodium was eluted with a solution comprising 90% v/v Methanol and 10% v/v water.

Figure 3:
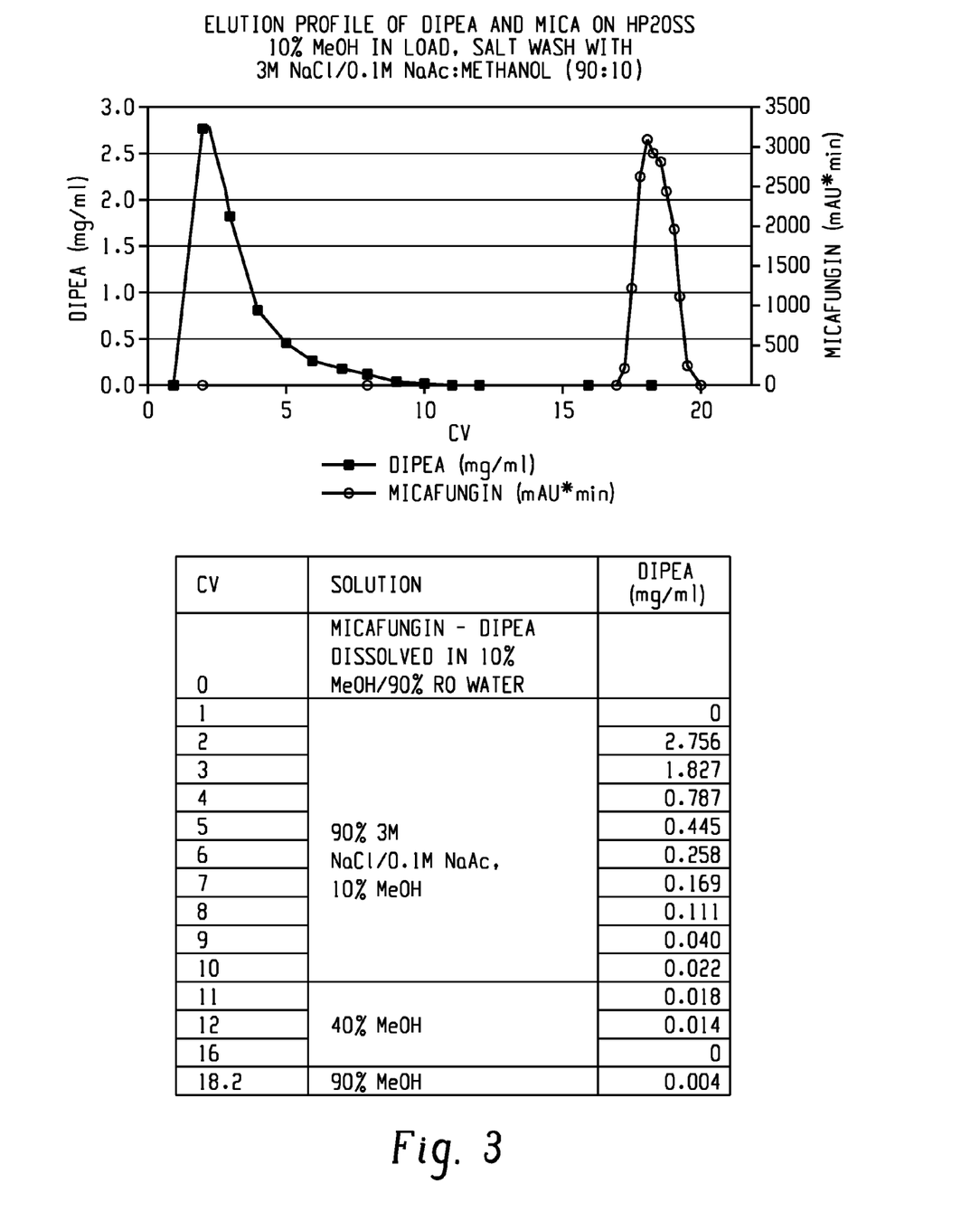

As seen in FIG. 3, the Micafungin sodium solution eluted at 18-20 CV is sufficiently free of DIPEA Example 4

Organic Solvent in Load

An aqueous solution comprising a crude Micafungin DIPEA salt and 10% v/v Methanol was applied to a HP20SS column.

The column was first washed with an aqueous solution comprising 3M NaCl/0.1M NaAc pH 5.5.

The column was then washed with an aqueous solution comprising 40% v/v Methanol.

Micafungin sodium was eluted with a solution comprising 90% v/v Methanol and 10% v/v water.

Figure 4:
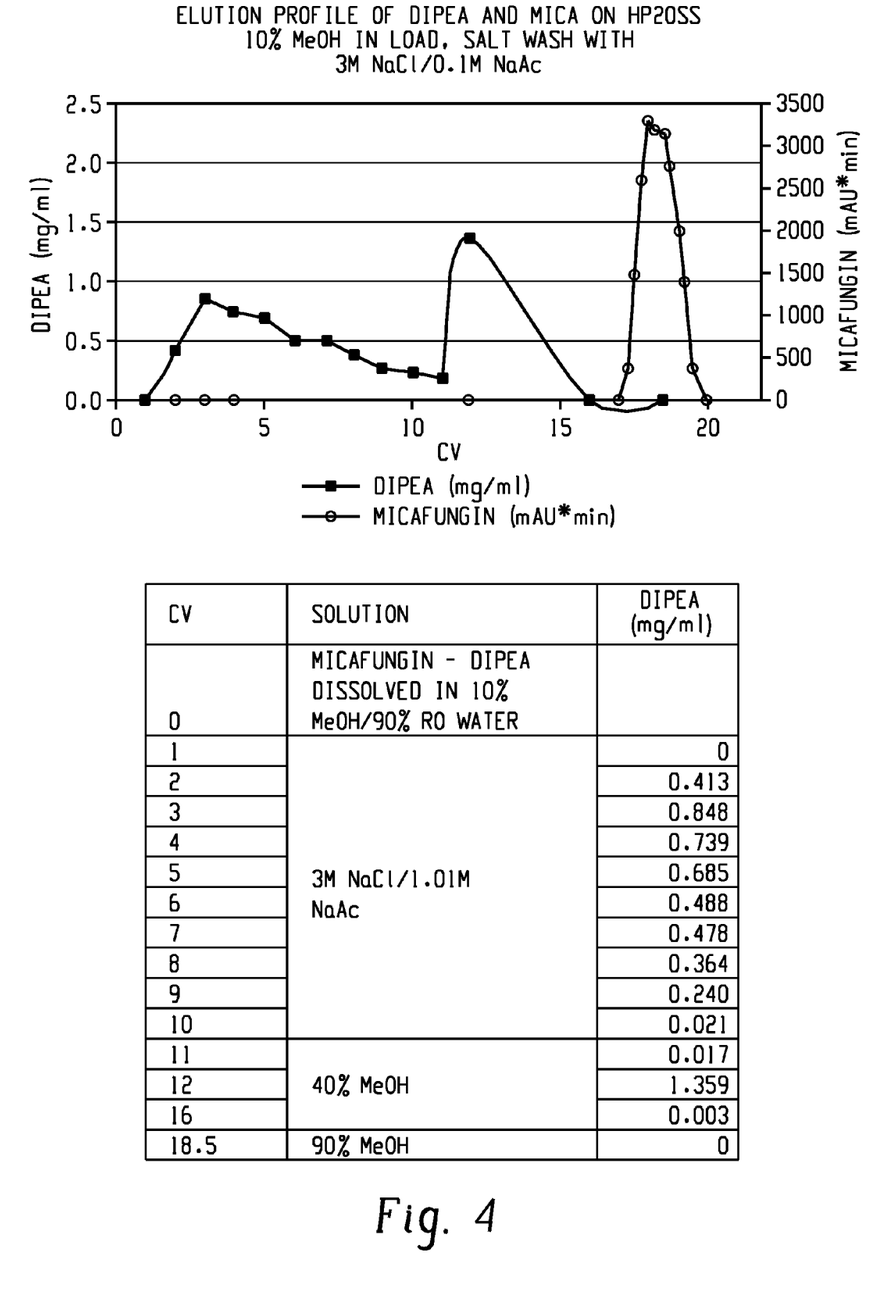

As seen in FIG. 4, the Micafungin sodium solution eluted at 18-20 CV is substantially free of DIPEA Example 5

No Organic Solvent in Load

An aqueous solution comprising a crude Micafungin DIPEA salt and 3M Sodium chloride, 0.1 M Sodium acetate, pH 5.5 was applied to a HP20SS column.

The column was first washed with an aqueous solution comprising 3M NaCl/0.1M NaAc pH 5.5.

The column was then washed with an aqueous solution comprising 40% v/v Methanol.

Micafungin sodium was eluted with a solution comprising 90% v/v Methanol and 10% v/v water.

Figure 5:
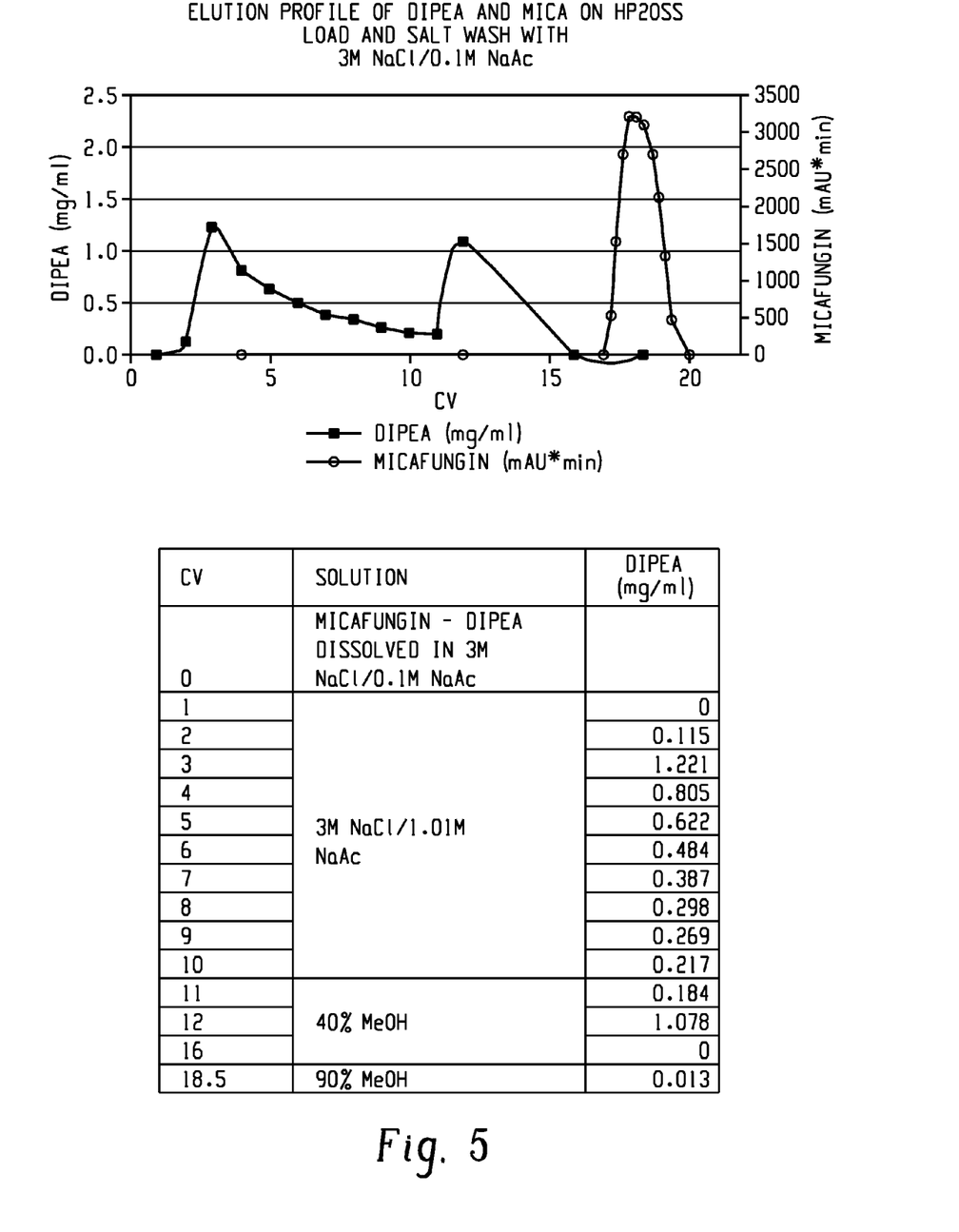

As seen in FIG. 5, the Micafungin sodium solution eluted at 18-20 CV is sufficiently free of DIPEA Example 6

No Organic Solvent in Load

An aqueous solution comprising crude Micafungin DIPEA salt was applied to a HP20SS column.

The column was first washed with an aqueous solution comprising 3M NaCl/0.1M NaAc pH 5.5

The column was then washed with an aqueous solution comprising 40% v/v Methanol.

Micafungin sodium was eluted with a solution comprising 90% v/v Methanol and 10% v/v water.

Figure 6:
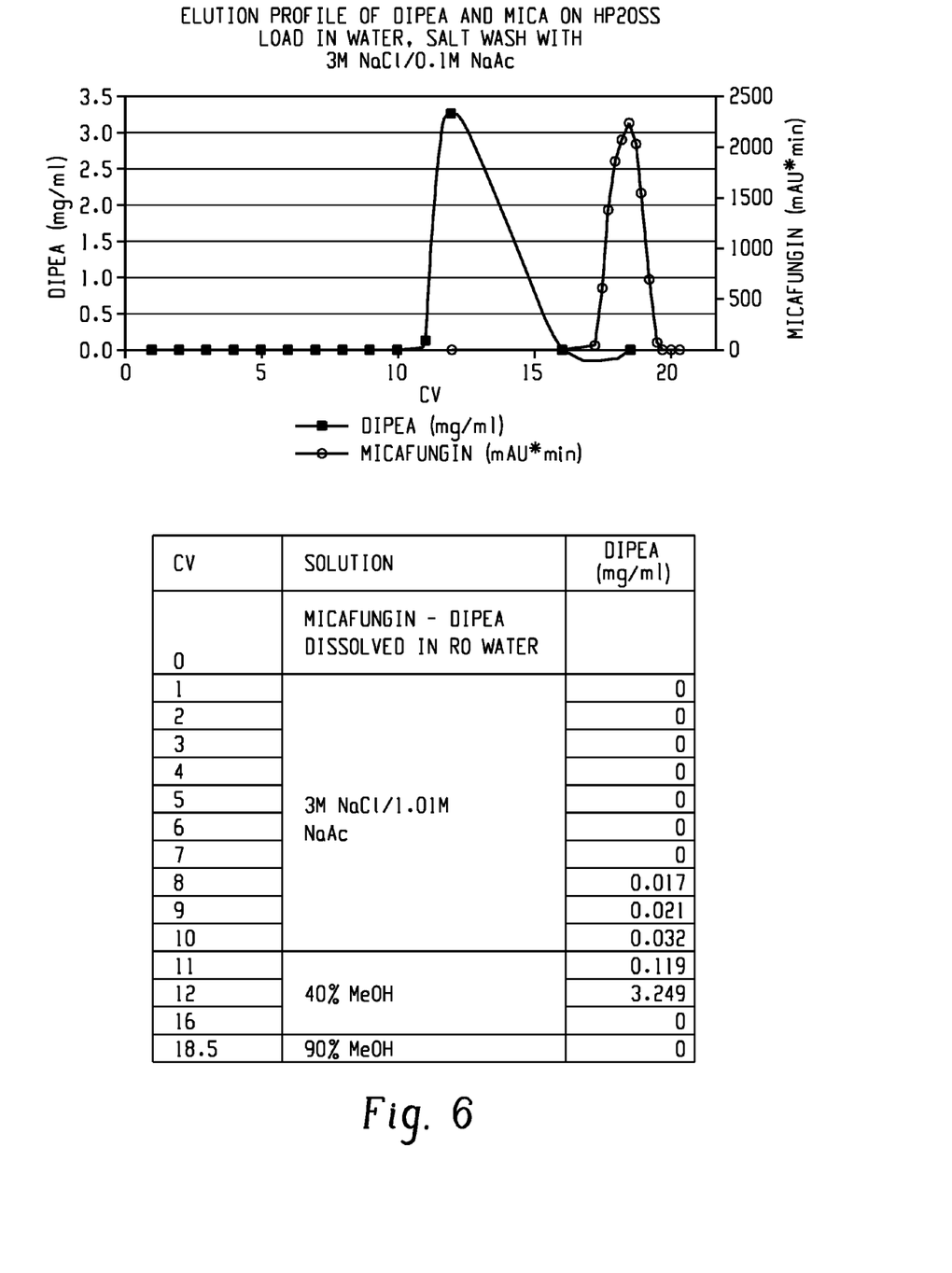

As seen in FIG. 6, the Micafungin sodium solution eluted at 18-20 CV is substantially free of DIPEA Example 7

Organic Solvent in Load and Wash

An aqueous solution comprising crude Micafungin DIPEA salt and 10% v/v Methanol was applied to a HP20SS column.

The column was first washed with an aqueous solution comprising 80% v/v 3M NaCl/0.1M NaAc pH 5.5 and 20% v/v Methanol.

The column was then washed with an aqueous solution comprising 70% v/v 3M Sodium chloride, 0.1 M Sodium acetate, pH 5.5 and 30% v/v Methanol.

The column was then washed with an aqueous solution comprising 40% v/v Methanol.

Micafungin sodium was eluted with a solution comprising 90% v/v Methanol and 10% v/v water.

Figure 7:
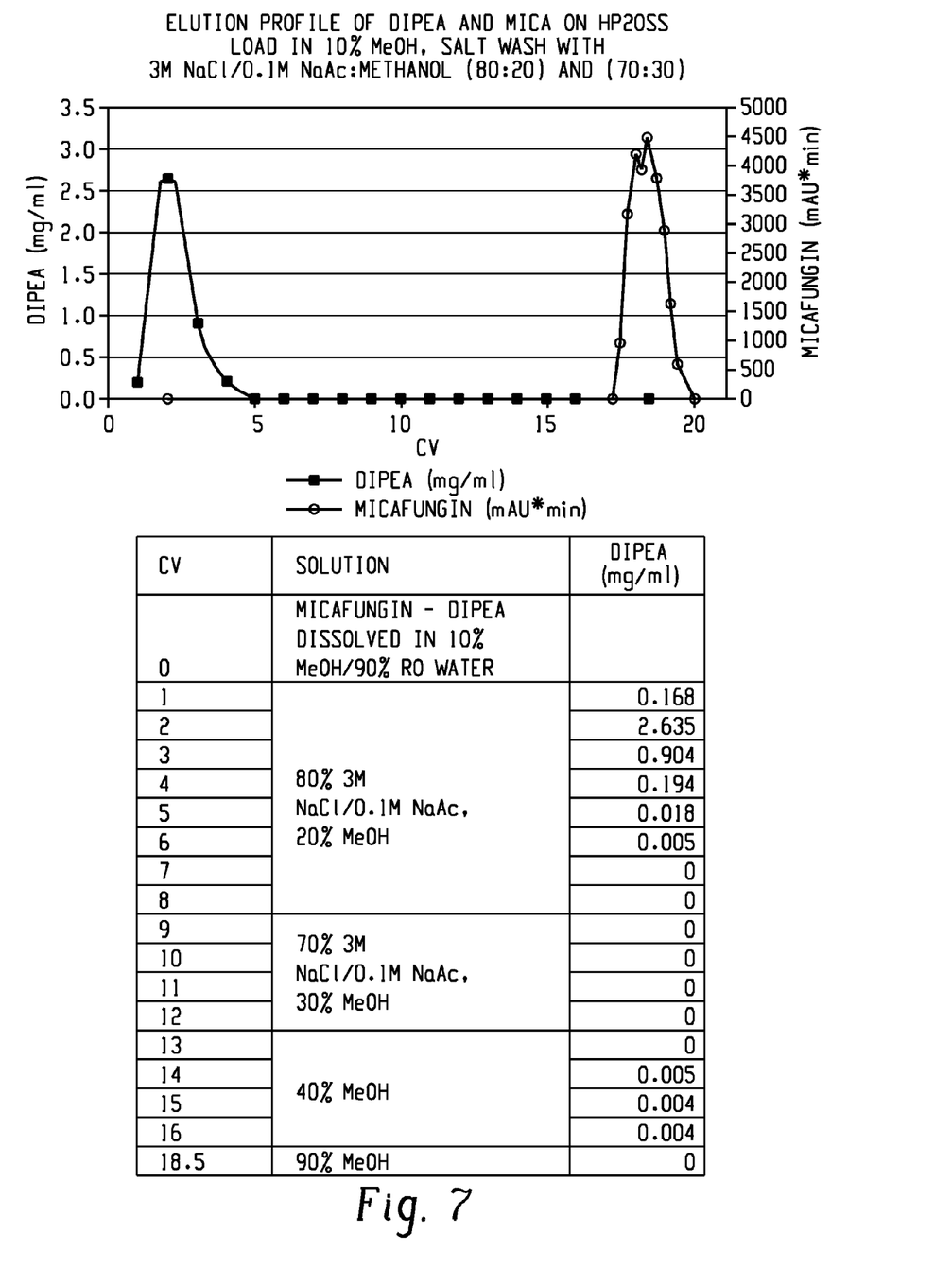

As seen in FIG. 7, the Micafungin sodium solution eluted at 18-20 CV is substantially free of DIPEA Example 8

Organic Solvent in Load and Wash

An aqueous solution comprising crude Micafungin DIPEA salt and 10% v/v Methanol was applied to a HP20SS column.

The column was first washed with an aqueous solution comprising 60% v/v 3M NaCl/0.1M NaAc pH 5.5 and 40% v/v Methanol.

The column was then washed with an aqueous solution 40% v/v Methanol

Micafungin sodium was eluted with a solution comprising 90% v/v Methanol and 10% v/v water.

Figure 8:
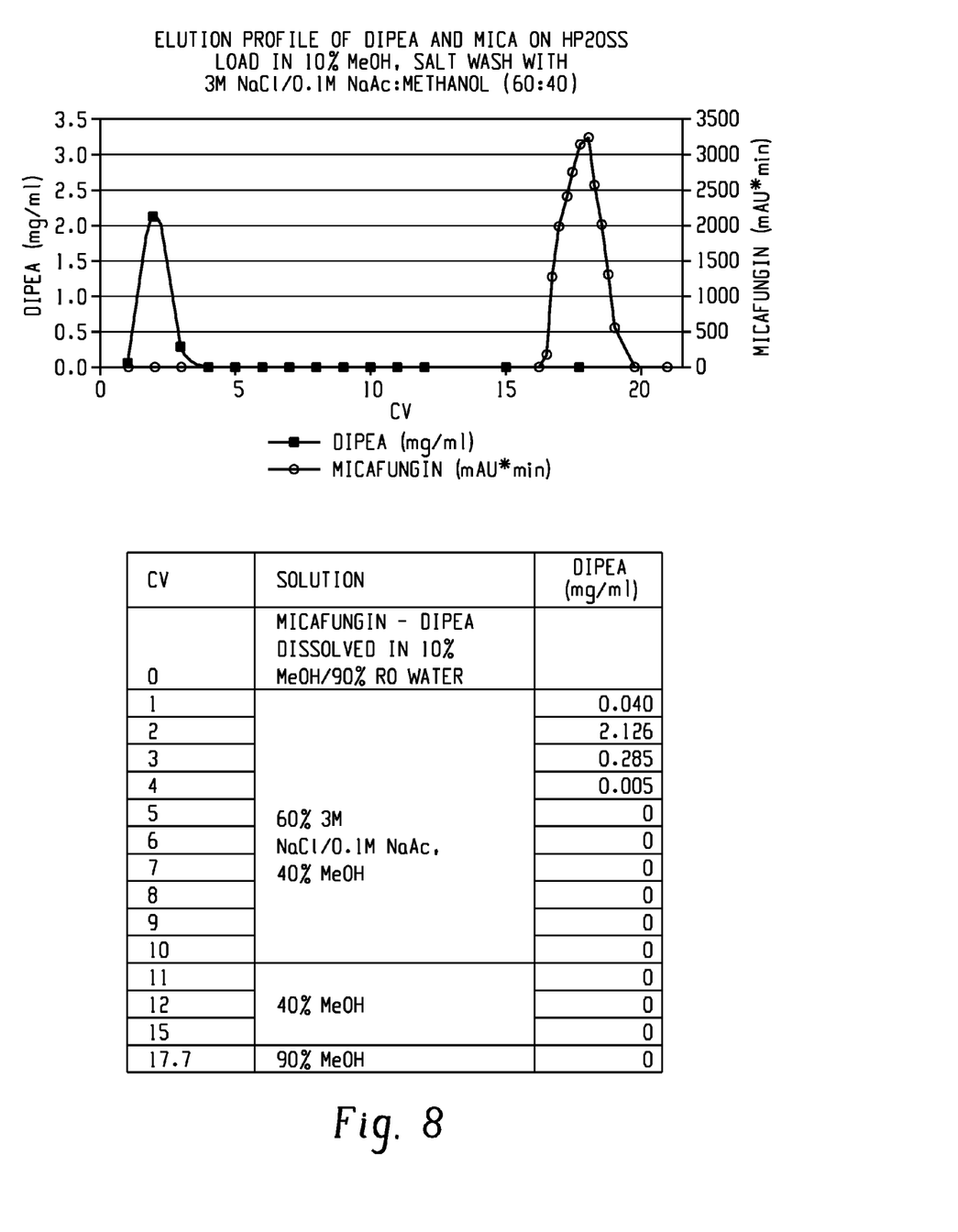

As seen in FIG. 8, the Micafungin sodium solution eluted at 18-20 CV is substantially free of DIPEA Example 9

Organic Solvent in Load and Wash

A hydrophobic resin, HP20SS (Diaion), was packed into a chromatography column (72 ml, i.d 2.6 cm). 5.4 g Micafungin starting material (100 mg Micafungin/ml) was added to the column (2.4 ml/min).

An aqueous solution comprising crude Micafungin DIPEA salt and 10% v/v Methanol was applied to a HP20SS column (54 ml).

The column was first washed with an aqueous solution comprising 80% v/v 3M NaCl/0.1M NaAc pH 5.5 and 20% v/v Methanol (576 ml).

The column was then washed with an aqueous solution 40% v/v Methanol (288 ml)

Micafungin sodium was eluted with a solution comprising 90% v/v Methanol and 10% v/v water.

Figure 9:
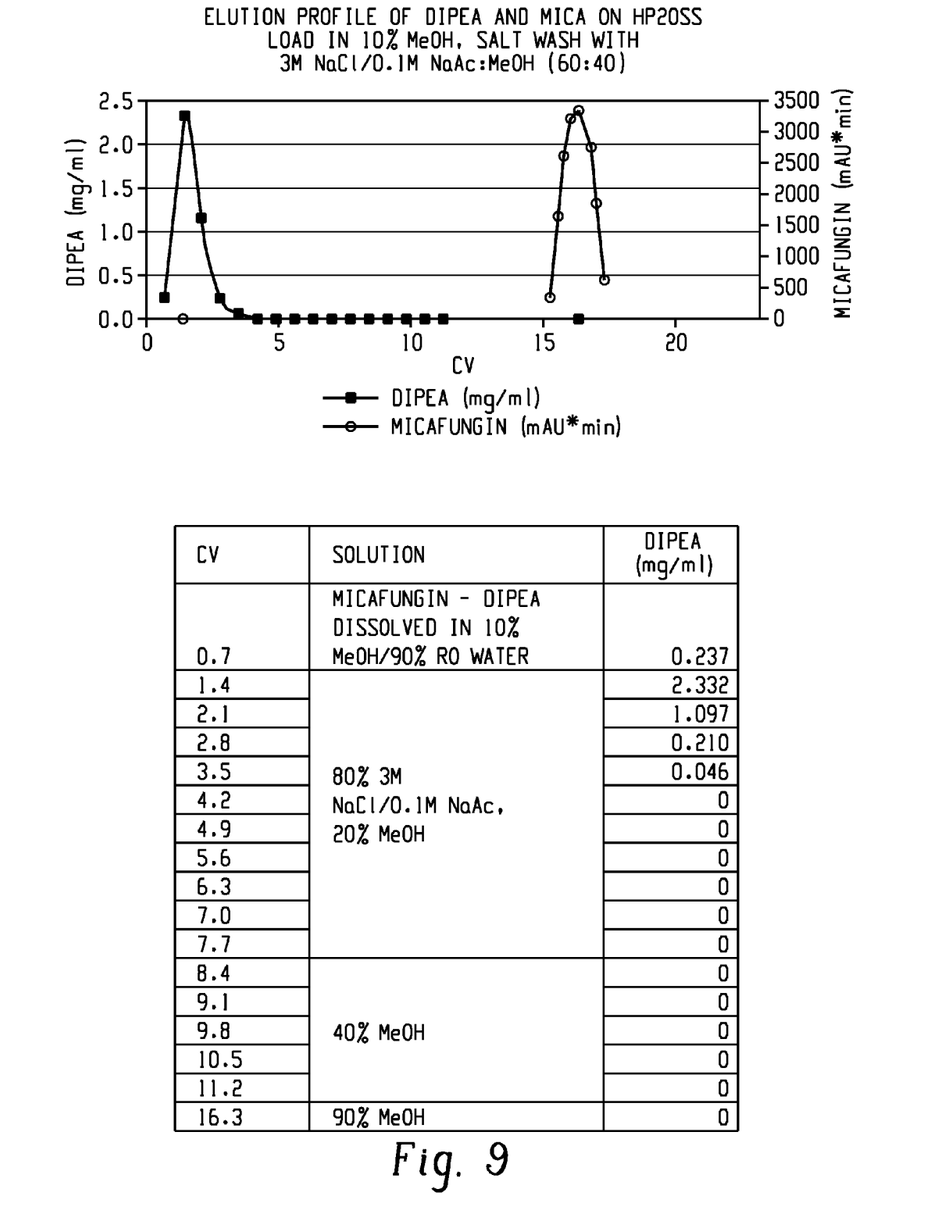

As seen in FIG. 9, the Micafungin sodium solution eluted at 15-17 CV is substantially free of DIPEA.

The invention claimed is:

1. A method for producing a pharmaceutically acceptable Micafungin salt comprising the steps of:
   a) applying a Micafungin starting material to a hydrophobic adsorbent resin support, wherein the Micafungin starting material comprises a Micafungin salt and the Micafungin is adsorbed to the hydrophobic adsorbent resin support;
   b) exposing the adsorbed Micafungin to an aqueous solution of a dissolved pharmaceutically acceptable salt to produce a pharmaceutically acceptable salt of Micafungin;
   c) washing the adsorbed Micafungin with a washing solution; and
   d) eluting the pharmaceutically acceptable salt of Micafungin with an elution solution comprising a water miscible organic solvent;
   provided that at least one of
   i) the Micafungin starting material in step a) or
   ii) the aqueous solution of the dissolved pharmaceutically acceptable salt in step b)
   comprises a water miscible organic solvent,
   wherein the Micafungin salt and the pharmaceutically acceptable salt of Micafungin are different.

2. The method according to claim 1, wherein the washing solution in step c) is an aqueous solution comprising a water miscible organic solvent.

3. The method according to claim 1, wherein the starting material in step a) comprises a water miscible organic solvent in the range of 0-30% v/v.

4. The method according to claim 3, wherein the starting material in step a) comprises a water miscible organic solvent in the range of 5-15% v/v.

5. The method according to claim 3, wherein the starting material in step a) comprises a water miscible organic solvent in an amount of 10% v/v.

6. The method according to claim 1, wherein the aqueous solution in step b) comprises a water miscible organic solvent in an amount of 0-40% v/v.

7. The method according to claim 6, wherein the aqueous solution in step b) comprises a water miscible organic solvent at 20% v/v.

8. The method according to claim 1, wherein the water miscible organic solvent is selected from the group consisting of branched or non-branched C1-C3 alcohols, C3-C6 ketones and polar aprotic organic solvents.

9. The method according to claim 8, wherein the water miscible organic solvent is selected from the group consisting of methanol, ethanol, propanol, isopropanol, acetone and acetonitrile.

10. The method according to claim 9, wherein the elution solution in step d)
    comprises at least 30% v/v acetonitrile as a water miscible organic solvent.

11. The method according to claim 9, wherein the water miscible organic solvent is methanol.

12. The method according to claim 11, wherein the elution solution in step d)
    comprises at least 70% v/v methanol.

13. The method according to claim 1, wherein the starting material in step a), the aqueous solution in step b), the washing solution in step c), and the elution solution in step d) comprises a water miscible organic solvent.

14. The method according to claim 1, wherein the pharmaceutically acceptable salt of Micafungin is the sodium salt, and the resin is a styrene-divinyl benzene resin, and the Micafungin starting material comprises Micafungin DIPEA and 10% v/v Methanol, and the aqueous solution in step b) comprises 20% v/v methanol and 80% v/v 3M NaCl, 0.1M NaCH$_3$COO and the solution in step c) comprises 40% v/v methanol and the solution in step d) comprises 90% v/v methanol.

15. A method for producing a pharmaceutically acceptable Micafungin salt comprising the steps of:
    a) applying a Micafungin starting material to a hydrophobic adsorbent resin support, wherein the Micafungin starting material comprises a Micafungin salt that is adsorbed to the hydrophobic adsorbent resin support;
    b) exposing the adsorbed Micafungin to an aqueous solution of a dissolved pharmaceutically acceptable salt to produce a pharmaceutically acceptable salt of Micafungin;
    c) optionally exposing the adsorbed Micafungin obtained in b) to an aqueous solution comprising a water miscible organic solvent one or more times for the removal of impurities;
    d) eluting the pharmaceutically acceptable salt of Micafungin with an elution solution comprising a water miscible organic solvent;
    provided that when step c) is not performed, then the Micafungin starting material and/or the aqueous solution in step b) comprises a water miscible organic solvent.

16. The method according to claim 1, wherein the Micafungin starting material or the aqueous solution in step b) comprises 2-30% v/v of a water miscible organic solvent.

17. The method according to claim 1, wherein the Micafungin starting material and the aqueous solution in step b) comprises 2-30% v/v of a water miscible organic solvent.

18. The method according to claim 1, wherein the washing solution in step c) comprises 30-50% v/v of a water miscible organic solvent.

19. The method according to claim 1, wherein the Micafungin salt in the Micafungin starting material is Micafungin DIPEA.

20. The method according to claim 1, wherein the resin is a synthetic resin in the form of porous beads comprising styrene-divinyl benzene resin.

21. The method according to claim 1, wherein the Micafungin starting material and the aqueous solution in step b) comprise a water miscible organic solvent.

22. The method according to claim 1, wherein the Micafungin starting material and the aqueous solution in step b) comprise methanol.

23. The method according to claim 1, wherein the water miscible organic solvent present in the Micafungin starting material and/or the aqueous solution in step b) is methanol.

24. The method according to claim 1, wherein the aqueous solution in step b) comprises methanol.

* * * * *